United States Patent
Niedospial, Jr. et al.

(10) Patent No.: US 6,206,859 B1
(45) Date of Patent: Mar. 27, 2001

(54) SELF-ALIGNING PLUNGER ROD

(75) Inventors: John J. Niedospial, Jr., Burlington; Ernest Balestracci, Iselin, both of NJ (US)

(73) Assignee: Bracco Diagnostics, Inc., Princeton, NJ (US)

( * ) Notice: Subject to any disclaimer, the term of this patent is extended or adjusted under 35 U.S.C. 154(b) by 0 days.

(21) Appl. No.: 09/546,342

(22) Filed: Apr. 10, 2000

Related U.S. Application Data

(63) Continuation-in-part of application No. 09/527,334, filed on Mar. 17, 2000, now Pat. No. 6,142,978, which is a continuation-in-part of application No. 09/490,272, filed on Jan. 24, 2000.

(51) Int. Cl.$^7$ ................................................. A61M 5/315
(52) U.S. Cl. .............................................................. 604/220
(58) Field of Search ................................... 604/218–220, 604/221, 222, 228, 230, 235

(56) References Cited

U.S. PATENT DOCUMENTS

| | | | |
|---|---|---|---|
| 4,543,093 | 9/1985 | Christinger | 604/228 |
| 4,840,616 | * 6/1989 | Banks | 604/218 |
| 4,890,626 | * 1/1990 | Wang | 604/220 |
| 5,215,536 | * 6/1993 | Lampropoulos et al. | 604/187 |
| 5,222,942 | 6/1993 | Bader | 604/110 |
| 5,358,497 | * 10/1994 | Dorsey et al. | 604/220 |
| 5,485,853 | * 1/1996 | Stubbs | 604/220 |
| 5,700,247 | 12/1997 | Grimard et al. | 604/220 |
| 6,030,367 | * 2/2000 | Balestracci | 604/218 |

FOREIGN PATENT DOCUMENTS

| | | | |
|---|---|---|---|
| WO 91/00114 | 1/1991 | (WO) | 604/218 |
| WO 93/09827 | 5/1993 | (WO) | 604/229 |

* cited by examiner

Primary Examiner—Sharon Kennedy
(74) Attorney, Agent, or Firm—Imre Balogh

(57) ABSTRACT

A self-aligning reinforced plunger rod and a non-elastomeric plastic plunger insert assembly for use with an elastomeric plunger in a cartridge or syringe barrel, the plunger rod having a first, second, third and fourth sides, a distal end with an end disc, a proximal end with a thumb rest, a central reinforcing disc at the midpoint between the end disc and the thumb rest, and a plunger rod tip integral with the end disc and having a neck portion and a ball portion for engagement with a cavity in the non-elastomeric plastic plunger insert. Connecting the end disc and thumb rest there are: four longitudinal radially extending rectangular vanes spaced about 90° from each other; on the first side of the plunger rod a first pair of longitudinal radially extending reinforcing vanes, and a second pair of longitudinal radially extending reinforcing vanes; on the third side opposite to the first side of the plunger rod, a first pair of longitudinal radially extending reinforcing vanes, and a second pair of longitudinal radially extending reinforcing vanes; each of the first pair and each of the second pair of longitudinal radially extending reinforcing vanes on the first side of the plunger rod and each of the first pair and each of the second pair of the longitudinal radially extending reinforcing vanes on the third side of the plunger rod forms an obtuse triangle with one of the longitudinal radially extending reinforcing vanes; on the second side of the plunger rod, a first pair of longitudinal radially extending reinforcing vanes forms a two-dimensional hourglass-shape surface, and on the fourth side of the plunger rod, a second pair of longitudinal radially extending reinforcing vanes forms a two-dimensional hourglass-shape surface. The non-elastomeric plastic plunger insert contains a cavity defined by its inside surface to receive the plunger rod tip. The combination directs the force exerted on the plunger rod in an axial direction.

9 Claims, 20 Drawing Sheets

FIG. 1 - PRIOR ART
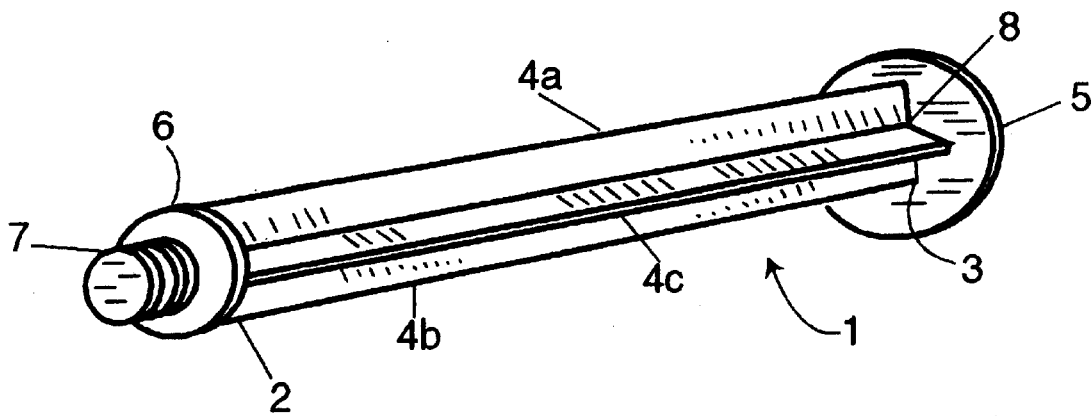
FIG. 2 - PRIOR ART
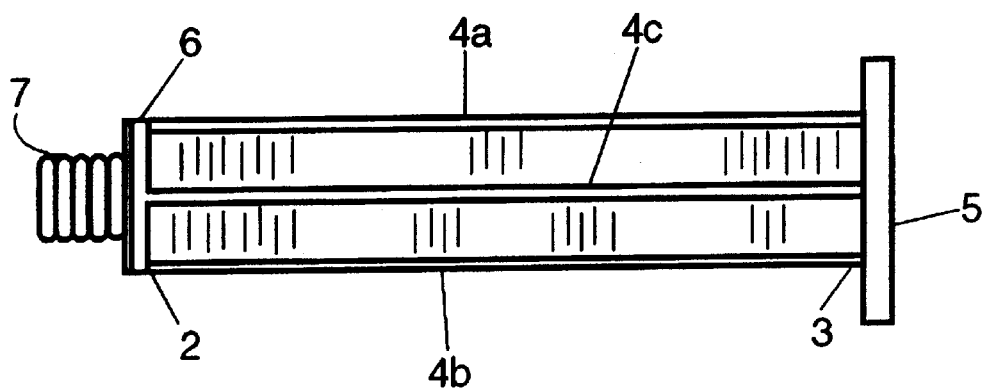

FIG. 3 - PRIOR ART
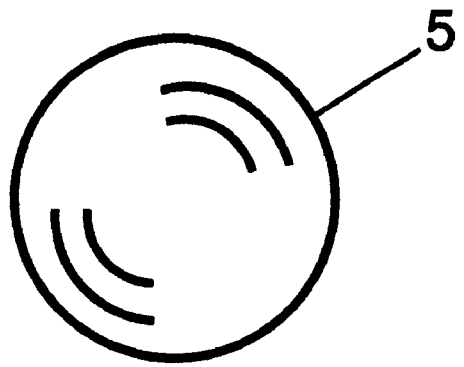
FIG. 4 - PRIOR ART
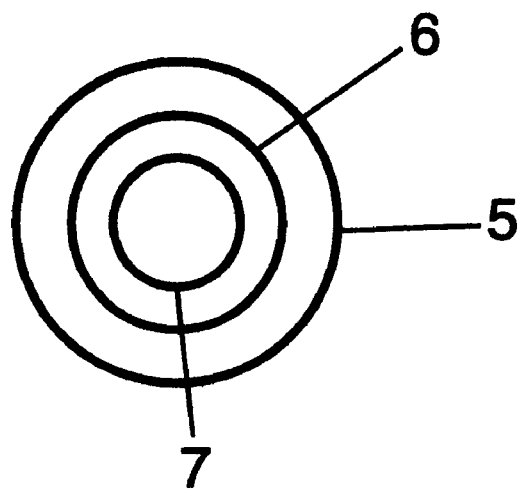

FIG. 13
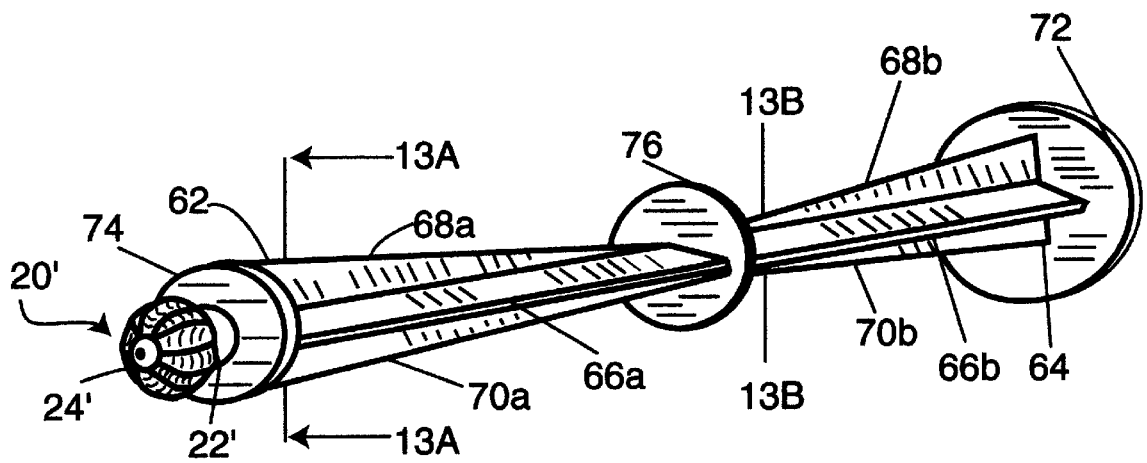
13A
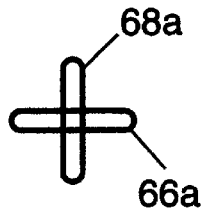
13B
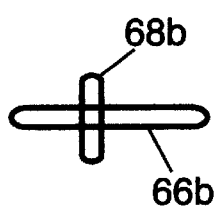

FIG. 18
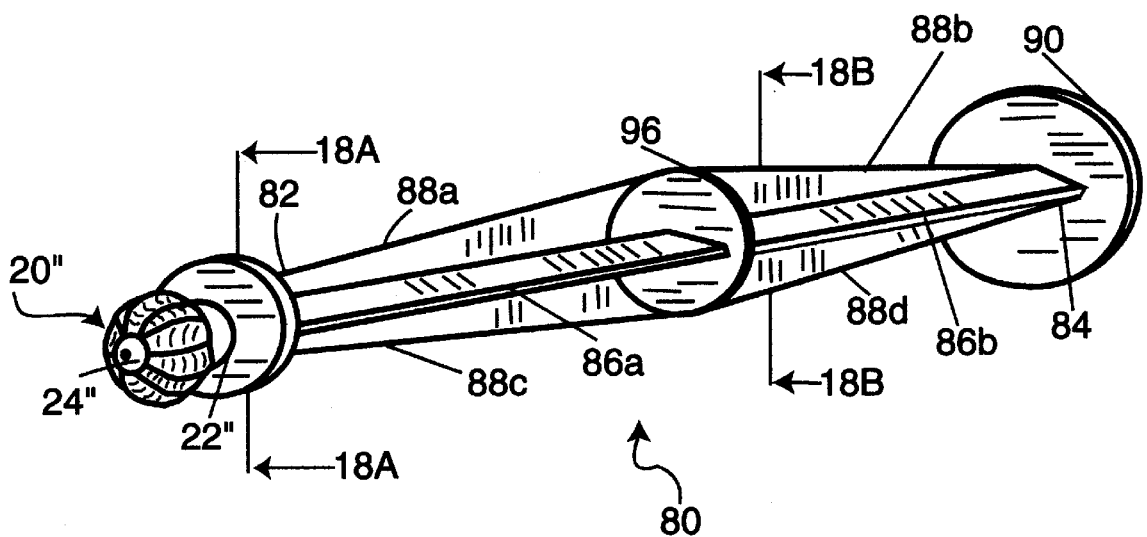
18A
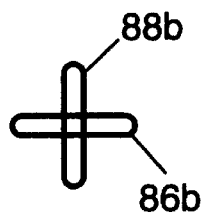
18B
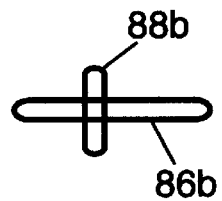

SELF-ALIGNING PLUNGER ROD

This application is a continuation-in-part of application Ser. No. 09/527,334 filed on Mar. 17, 2000, now U.S. Pat. No. 6,142,978 issued Nov. 7, 2000, which in turn is a continuation-in-part of application Ser. No. 09/490,272, filed on Jan. 24, 2000, now allowed.

BACKGROUND OF THE INVENTION

1. Field of the Invention

This invention relates to a self-aligning plunger rod for use in a syringe or cartridge barrel having a plunger and containing a parenteral solution therein, or in a syringe or cartridge which are empty and are to be filled with a parenteral solution by the user at the time of administration.

The present invention also relates to a plunger rod for use in a syringe or cartridge containing a parenteral solution therein intended to be dispensed from a power injector.

2. Reported Developments

Syringes and cartridges made of glass or polymeric materials for dispensing parenteral solutions or withdrawing biological fluids from a patient are well known in the prior art. They comprise a cylindrical barrel with a tapered portion at one end to which a needle or luer connector can be attached, and an open end which is stoppered by a plunger of a resilient thermoplastic or elastomeric material. The plunger serves the function of a stopper, when the barrel is filled with a fluid, or as a slidable member to expel the fluid from the barrel or withdraw a biological fluid from a patient or another source.

In order to expel fluid from the barrel or withdraw fluid into the barrel, the plunger is moved toward the distal end or the proximal end of the barrel by a plunger rod which is attachable to the plunger typically by screw threads. The user exerts a force, manually or by the use of a power injector, on the plunger rod to push or pull the plunger in the barrel. While the plunger rod does not contact the fluid in the barrel, it serves a very important function: it causes the plunger to move in an axial direction back and forth in the barrel when an external force is applied thereon.

The force applied to the plunger by the plunger rod should be perpendicular to the plunger so that the force exerted on the wall of the barrel by the plunger is uniform around the 360° of its cylindrical configuration. When the plunger rod flexes in the barrel, the direction of force on the plunger will not be uniform resulting in pressure points at certain areas of contact between the plunger and the inside wall of the barrel and, conversely, inadequate pressure points at other parts of the interface between the plunger and the inside wall of the barrel. Such pressure differences tend to allow leakage and difficulty in moving the plunger at an even rate in the barrel.

Typical prior art devices have fixed connections between plunger rods and plungers; they are either one-piece combinations of plunger rods and plungers or two-piece combinations wherein the plunger rods are threaded into the plungers. Some plungers are equipped with rigid plastic inserts having internal threads therein in order to support the elastomeric plunger heads and to engage the plunger rods and hold them in an axial orientation. Both approaches allow some movement of the plunger rods in a lateral direction which may result in leakage of the medical fluid from the syringe barrel.

Recognizing the importance of dimensional stability, the prior art has incorporated various stability enhancing means into plunger rods which include the following.

The assembly disclosed in U.S. Pat. No. 4,543,093 has a plunger rod, the central portion of which is almost as large as the inside diameter of the syringe barrel so that it will assist in keeping the plunger rod assembly concentrically aligned within the syringe barrel.

WO 93/09827 discloses a shank having a plurality of longitudinal and radially extending vanes. In one preferred embodiment the shank is provided with four vanes in an "X" pattern, while in another preferred embodiment, the shank is provided with three vanes forming a "Y" pattern.

U.S. Pat. Nos. 5,700,247 and 5,860,961 disclose plunger rods having a plurality of vanes or support ribs.

A common feature of these plunger rods is a shank extending between the distal and proximal ends of the plunger rods having vanes or support ribs thereon. The vanes or support ribs are identical with one another running longitudinally on the shank and extending radially therefrom. This feature is an improvement over typical plunger rods in that the plunger rods have limited flexibility in the lateral direction, thereby exerting pressure on the plunger surface in an axial direction. However, we have found that even limited flexibility of the plunger rods allow lateral movement of the plungers in syringe barrels. This lateral movement of the plunger rods attached to plungers can cause leakage of fluid from the syringe barrels.

An object of the present invention is to provide a plunger rod and plastic plunger insert combination which directs the force exerted on the plunger rod in an axial direction. The elastomeric plunger placed on the plastic plunger insert will exert a uniform force on the inside wall of the syringe barrel thereby preventing leakage of the fluid content from the syringe barrel.

Another object of the present invention is to provide a reinforced plunger rod in combination with a plastic plunger insert which may be used either manually or in a power injector. Reinforced plunger rods without plastic plunger inserts are disclosed in co-pending application Ser. No. 09/408,242 filed on Sep. 29, 1999 which is incorporated herein by reference.

SUMMARY OF THE INVENTION

In accordance with the present invention there is provided a plunger rod and plastic plunger insert combination having a self-aligning feature wherein the plunger rod tip fits into the socket of the plunger insert and freely glides therein. This feature allows the plunger rod tip to float in the socket of the plastic plunger insert and eliminates lateral pressure on the plastic plunger insert. The plastic plunger insert is equipped with an elastomeric plunger which may be of various configurations.

In the first embodiment of the present invention the self-aligning plunger rod and plastic plunger insert combination is provided which comprises:

a) a plunger rod having a distal end and a proximal end comprising:
longitudinal radially extending vanes;
a thumb rest at the proximal end;
a disc at the distal end; and
a plunger rod tip extending from the disc at the distal end designed to engage a plastic plunger insert, said plunger rod tip comprising a neck portion and a ball portion, the ball portion having slots therein extending axially from the neck portion;

b) a non-elastomeric plastic plunger insert comprising:
a cylindrical shaft having a distal end and a proximal end;
a cone-shaped head extending from the distal end of the cylindrical shaft having an inside surface and an outside surface;
a cavity in the cone-shaped head defined by a cylindrical rim and the inside surface of the cone-shaped head;
a plurality of tabs extending from the cylindrical rim into the cavity; and
a plurality of notches or openings between the tabs designed to receive the slotted ball portion of the plunger rod tip.

In use, the slots of the plunger rod tip are aligned with the notches or openings in the plastic insert. The ball portion of the plunger rod tip is inserted into the cavity of the plastic insert and rotated to engage the tabs of the plastic insert.

In a second embodiment of the present invention a reinforced plunger rod body is used in combination with the plunger rod tip and the plastic insert. The reinforced plunger rod body having a distal end and a proximal end comprises:
an end disc at the distal end;
a plunger rod tip extending from the end disc designed to engage a plastic plunger insert, said plunger rod tip comprising a neck portion and a ball portion, the ball portion having slots therein extending axially from the neck portion;
a thumb rest at the proximal end for facilitating exertion of external pressure on the plunger rod;
a reinforcing disc at about the longitudinal midpoint of the plunger rod;
a first pair of rectangular radially extending vanes connecting the end disc and the reinforcing disc;
a second pair of rectangular radially extending vanes connecting the reinforcing disc and the thumb rest,
a first pair of isosceles triangular radially extending vanes connecting the end disc and the reinforcing disc, wherein the smallest angle of the isosceles triangular vanes point toward the reinforcing disc; and
a second pair of isosceles triangular radially extending vanes connecting the reinforcing disc and the thumb rest, wherein the smallest angle of the isosceles triangular vanes point toward the reinforcing disc, wherein:
said first pair of said rectangular radially extending vanes and said first pair of said isosceles triangular radially extending vanes are integral with each other and with said end disc and said reinforcing disc; and
said second pair of said rectangular radially extending vanes and said second pair of said isosceles triangular radially extending vanes are integral with each other and with said reinforcing disc and said thumb rest.

In a third embodiment of the present invention, a reinforced plunger rod body of a different configuration from that of the reinforced plunger rod body of the second embodiment is used in combination with the plunger rod tip and the plastic insert.

The reinforced plunger rod having a distal end and a proximal end comprises:
an end disc at the distal end;
a plunger rod tip extending from the end disc designed to engage a plastic plunger insert, said plunger rod tip comprising a neck portion and a ball portion, the ball portion having slots therein extending axially from the neck portion;
a thumb rest at the proximal end for facilitating exertion of external pressure on the plunger rod;
a reinforcing disc at about the longitudinal midpoint of the plunger rod;
a first pair of rectangular radially extending vanes connecting the end disc and the reinforcing disc;
a second pair of rectangular radially extending vanes connecting the reinforcing disc and the thumb rest,
a first pair of isosceles triangular radially extending vanes connecting the end disc and the reinforcing disc, wherein the smallest angle of the isosceles triangular vanes point toward the reinforcing disc; and
a second pair of isosceles triangular radially extending vanes connecting the reinforcing disc and the thumb rest, wherein the smallest angle of the isosceles triangular vanes point toward the reinforcing disc, wherein:
said first pair of said rectangular radially extending vanes and said first pair of said isosceles triangular radially extending vanes are integral with each other and with said end disc and said reinforcing disc; and
said second pair of said rectangular radially extending vanes and said second pair of said isosceles triangular radially extending vanes are integral with each other and with said reinforcing disc and said thumb rest.

In use, the slots of the plunger rod tip are aligned with the notches or openings in the plastic insert. The ball portion of the plunger rod tip is inserted into the cavity of the plastic insert and rotated to engage the tabs of the plastic insert.

In the fourth embodiment of the present invention a self-aligning reinforced plunger rod and plastic plunger insert combination is provided which comprises:
a) a plunger rod having first, second, third and fourth sides, a distal end and a proximal end comprising:
an end disc at the distal end;
a thumb rest at the proximal end for facilitating exertion of external pressure on the plunger rod;
a plunger rod tip extending from the end disc adapted to engage a plastic plunger insert, said plunger rod tip comprising a neck portion and a ball portion, the ball portion having slots therein extending axially from the neck portion;
four longitudinal radially extending rectangular vanes spaced about 90° from each other and connected to the end disc and to the thumb rest;
on the first side of said plunger rod:
a first pair of longitudinal radially extending reinforcing vanes;
a second pair of longitudinal radially extending reinforcing vanes, both the first pair and the second pair of longitudinal radially extending reinforcing vanes being connected to the end disc and to the thumb rest;
on the third side opposite to said first side of said plunger rod;
a first pair of longitudinal radially extending reinforcing vanes;
a second pair of longitudinal radially extending reinforcing vanes, both the first pair and the second pair of longitudinal radially extending reinforcing vanes being connected to the end disc and to the thumb rest,
wherein:
each of said first and second pairs of longitudinal radially extending rectangular vanes on the first side of the plunger rod, and each of said first and second pairs of the longitudinal radially extending reinforcing vanes on the third side of said plunger rod forms an obtuse triangle with one of the longitudinal radially extending rectangular vanes, wherein the obtuse angle of the so-formed triangle is at the midpoint between the end disc and the thumb rest;

on the second side of said plunger rod:
a first pair of longitudinal radially extending support vanes forming a two-dimensional hourglass-shape surface extending from the end disc to the thumb rest; and on the fourth side of said plunger rod:
a second pair of longitudinal radially extending supporting vanes forming a two-dimensional hourglass-shape surface extending from the end disc to the thumb rest, b) a non-elastomeric plastic plunger insert comprising:
a cylindrical shaft having a distal end and a proximal end;
a cone-shaped head extending from the distal end of the cylindrical shaft having an inside surface and an outside surface;
a cavity in the cone-shaped head defined by a cylindrical rim and the inside surface of the cone-shaped head;
a plurality of tabs extending from the cylindrical rim into the cavity; and
a plurality of notches or openings between the tabs designed to receive the slotted ball portion of the plunger rod tip.

In use, the slots of the plunger rod tip are aligned with the notches or openings in the plastic insert. The ball portion of the plunger rod tip is inserted into the cavity of the plastic insert and rotated to engage the tabs of the plastic insert.

In the fifth embodiment of the present invention, a self-aligning reinforced plunger rod and plastic plunger insert combination is provided which comprises:

a) a plunger rod having first, second, third and fourth sides, a distal end, and a proximal end comprising:
an end disc at the distal end;
a plunger rod tip extending from the end disc designed to engage a plastic plunger insert, said plunger rod tip comprising a neck portion and a ball portion, the ball portion having slots therein extending axially from the neck portion;
a thumb rest at the proximal end for facilitating exertion of external pressure on the plunger rod;
a central disc at about the midpoint between the end disc and the thumb rest to provide additional reinforcement between the end disc and the thumb rest;
four longitudinal radially extending rectangular vanes spaced 90° from each other and connected to the end disc, the central disc, and to the thumb rest;

on the first side of said plunger rod:
a first pair of longitudinal radially extending reinforcing vanes;
a second pair of longitudinal radially extending reinforcing vanes, both the first pair and the second pair of longitudinal radially extending reinforcing vanes being connected to the end disc, the central disc, and to said thumb rest;

on the third side opposite to said first side of said plunger rod;
a first pair of longitudinal radially extending reinforcing vanes;
a second pair of longitudinal radially extending reinforcing vanes, both the first pair the second pair of longitudinal radially extending reinforcing vanes being connected to the end disc, the central disc, and to the thumb rest;

wherein:
each of said first and second pairs of the longitudinal radially extending reinforcing vanes on the first side of the plunger rod, and each of said first and second pairs of the longitudinal radially extending reinforcing vanes on the third side of said plunger rod forms an obtuse triangle with one of the longitudinal radially extending rectangular vanes, wherein the obtuse angle of the so-formed triangle is at the midpoint between the end disc and thumb rest;

on the second side of said plunger rod:
a first pair of longitudinal radially extending reinforcing vanes forming a two-dimensional hourglass-shape surface extending from the end disc to the central disc, and from the central disc to the thumb rest; and on the fourth side of said plunger rod:
a second pair of longitudinal radially extending reinforcing vanes forming a two-dimensional hourglass-shape surface extending from the end disc to the central disc, and from the central disc to the thumb rest;

b) a non-elastomeric plastic plunger insert comprising:
a cylindrical shaft having a distal end and a proximal end;
a cone-shaped head extending from the distal end of said cylindrical shaft having an inside surface and an outside surface;
a cavity in the cone-shaped head defined by a cylindrical rim and the inside surface of the cone-shaped head;
a plurality of tabs extending from the cylindrical rim into the cavity; and
a plurality of notches or openings between the tabs designed to receive the slotted ball portion of the plunger rod tip.

In use, the slots of the plunger rod tip are aligned with the notches or openings in the plastic insert. The ball portion of the plunger rod tip is inserted into the cavity of the plastic insert and rotated to engage the tabs of the plastic insert.

BRIEF DESCRIPTION OF THE DRAWINGS

FIG. 1 is a prospective view of a prior art plunger rod;

FIG. 2 is a side elevational view thereof,

FIG. 3 is a bottom plan view thereof,

FIG. 4 is a top plan view thereof;

FIG. 12A is an enlarged view of one of the cylindrical notches in the outside surface of the ball portion of the plastic insert shown in FIG. 12;

FIG. 13 is a perspective view of one embodiment of the present invention showing a reinforced plunger rod;

FIG. 13A is a cross-sectional view of the reinforced plunger rod taken along the line 13A—13A of FIG. 13;

FIG. 13B is another cross-sectional view of the reinforced plunger rod taken along the line 13B—13B of FIG. 13;

FIG. 18 is a perspective view of another embodiment of the present invention showing a reinforced plunger rod;

FIG. 18A is a cross-sectional view of the reinforced plunger rod taken along the line 18A—18A of FIG. 18;

FIG. 18B is a cross-sectional view of the reinforced plunger rod taken along the line 18B—18B of FIG. 18;

DETAILED DESCRIPTION OF THE INVENTION

Figure 5:
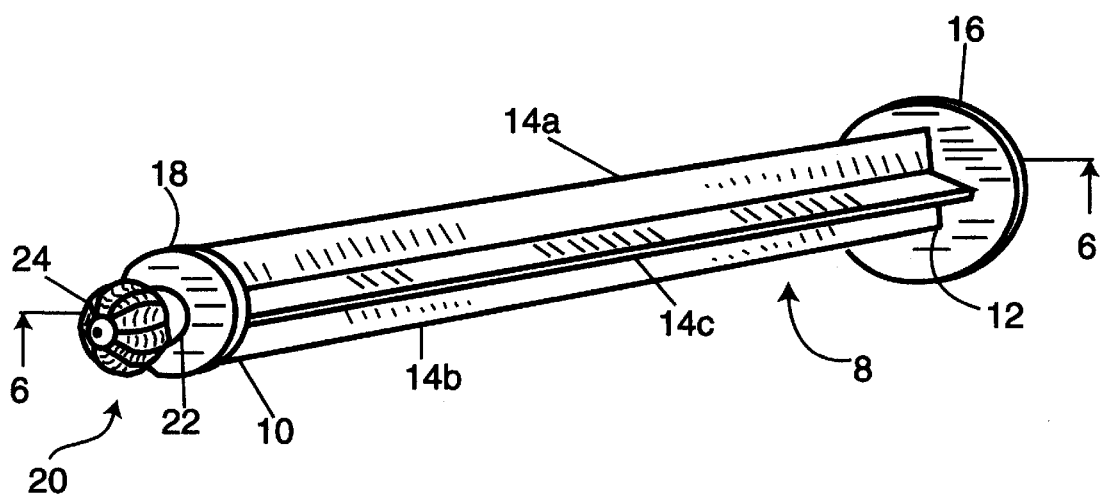
FIG. 5 is a perspective view of the plunger rod of the present invention.
Figure 6:
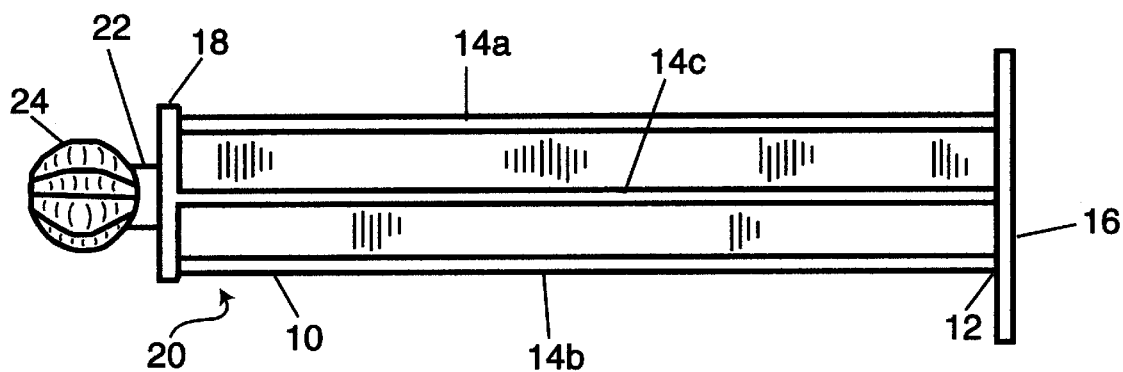
FIG. 6 is a cross-sectional view thereof taken along the line 6—6 of FIG. 5.
Figure 7:
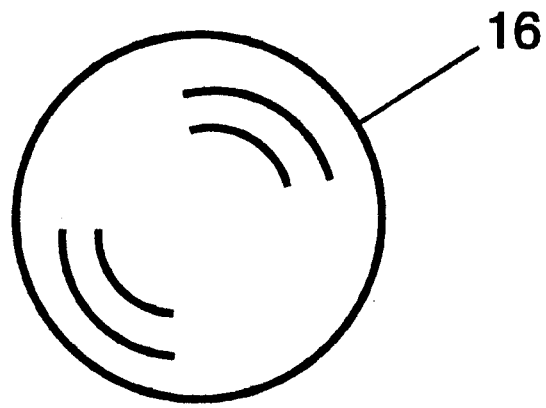
FIG. 7 is a bottom plan view thereof.

In the drawings, like numerals with ', ", '", or $^{vi}$ denote the same or similar parts of the device in different embodiments or views of the present invention.

Referring to FIGS. 1–4, a typical prior art plunger rod is shown in perspective, side elevational, bottom plan, and top plan views. Plunger rod 1 having a distal end 2 and a proximal end 3 comprises: longitudinal and radially extending vanes 4a, 4b, 4c and 4d (4d is hidden in the perspective view); a thumb rest 5 at the proximal end and a disc 6 at the distal end 2 of the plunger rod; and a screw threaded member 7 extending from disc 6 designed to engage a plunger. Vanes 4a, 4b, 4c and 4d are equivalent to one another extending from thumb rest 5 to disc 6. These vanes meeting at the center 8 of the plunger rod are of rectangular configuration.

The plunger rod is threaded into an elastomeric plunger which also contains thread means for engagement with the plunger rod. When the plunger rod joined with the plunger is inserted into the barrel of a syringe or cartridge to expel medical fluid contained in the barrel, the manual force exerted on the plunger rod will move the plunger towards the distal end of the barrel. However, this manual force has two components: a large force in the axial direction; and a smaller force in the lateral direction. This smaller force tends to cause non-uniform pressure points at certain areas of contact between the plunger and the inside wall of the barrel. Such pressure differences tend to allow leakage of the content of the barrel and creates difficulty in moving the plunger at an even rate in the barrel.

We have now discovered a plunger rod and plastic plunger insert combination having a self-aligning feature wherein the plunger rod tip fits into the socket of the plunger insert and freely glides therein. This feature allows the plunger rod tip to float in the socket of the plastic plunger insert and eliminates lateral pressure on the plastic plunger insert. This and other advantageous features will be explained in the description of the invention in reference to the drawings.

Referring to FIGS. 5–8, showing perspective, side elevational, bottom and top plan views, there is shown a plunger rod 8 (generally designated) having a distal end 10 and a proximal end 12 comprising: longitudinal radially extending vanes 14a, 14b, 14c and 14d (14d is hidden); a thumb rest 16 at the proximal end, and a disc 18 at the distal end; and plunger rod tip 20 (generally designated) extending from disc 18 designed to engage a plastic insert. Plunger rod tip 20 is integral with disc 18 and comprises: a neck portion 22 and a ball portion 24, the ball portion having slots 24a, 24b, 24c and 24d therein extending axially from the neck portion.

Figure 9:
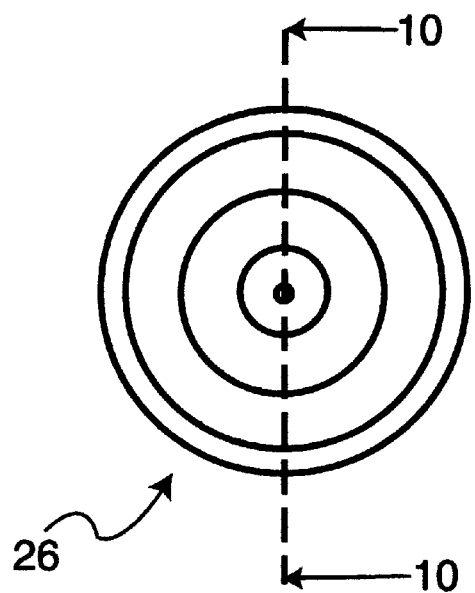
FIG. 9 is a top plan view of a plastic insert of the present invention which is to engage the plunger rod.
Figure 10:
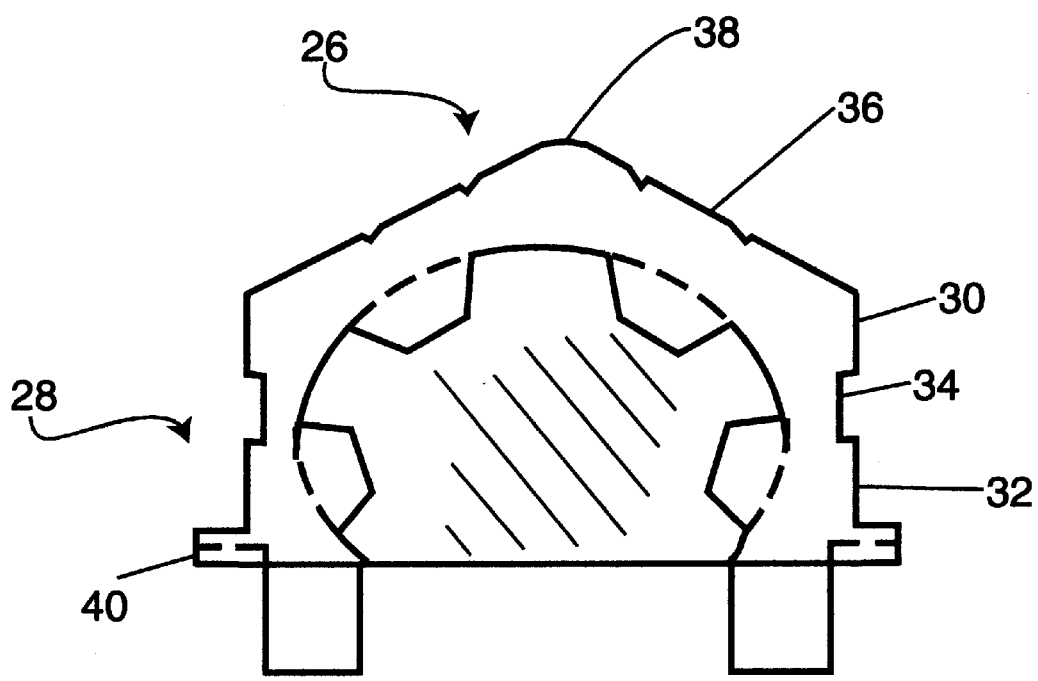
FIG. 10 is a cross-sectional view of the plastic insert taken along the line 10—10 of FIG. 9.

The self-aligning plunger rod 8 of the present invention is used in combination with a plastic insert, the top plan view of which is shown in FIG. 9. It is of a generally cone-shaped configuration best seen in FIG. 10 which is a cross-sectional view of the plastic insert, taken along the line 10—10 of FIG. 9. The plastic insert, generally designated by the numeral 26, comprises: a cylindrical shaft 28 having a distal end 30, and a proximal end 32; between the distal and proximal ends there is provided a cylindrical recess or groove 34; a cone-shaped head 36 extending from distal end 30 and terminating in zenith 38; and a cylindrical flange 40 extending from the proximal end 32.

Figure 11:
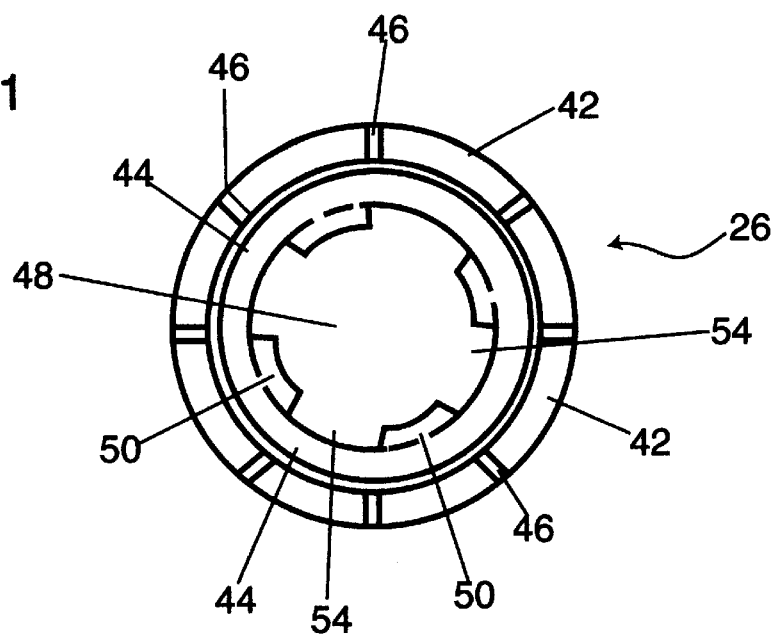
FIG. 11 is a bottom plan view of the plastic insert.

FIG. 11 shows a bottom plan view of the plastic insert 26 which comprises: a first cylindrical rim 42 constituting the underside of cylindrical flange 40; a second cylindrical rim 44 adjacent to said first cylindrical rim and projecting slightly above the horizontal surface of the first cylindrical rim; a plurality of reinforcing rods 46 connecting the first cylindrical rim 42 and the second cylindrical rim 44; a cavity 48 defined within said second cylindrical rim and the inside surface of the cone-shaped head 36; and a plurality of tabs 50 extending from the second cylindrical rim 44 into cavity 48. Between tabs 50 there are notches 52 to receive the slotted ball portion of the plunger rod tip.

Figure 8:
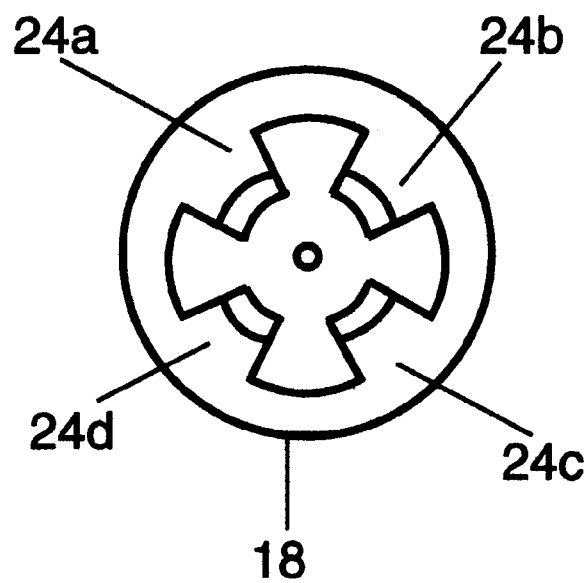
FIG. 8 is a top plan view thereof.

FIG. 11 shows: 8 reinforcing rods, however, less than 8 or more than 8 rods may be used; 4 tabs are shown, however, two or three tabs or more than four tabs may be used. Similarly, four slots are shown in FIG. 8 of the ball portion of the plunger rod tip.

However, more or less slots may be used as long as the number of slots in the ball portion match the number of tabs in the plastic insert 26.

Figure 12:
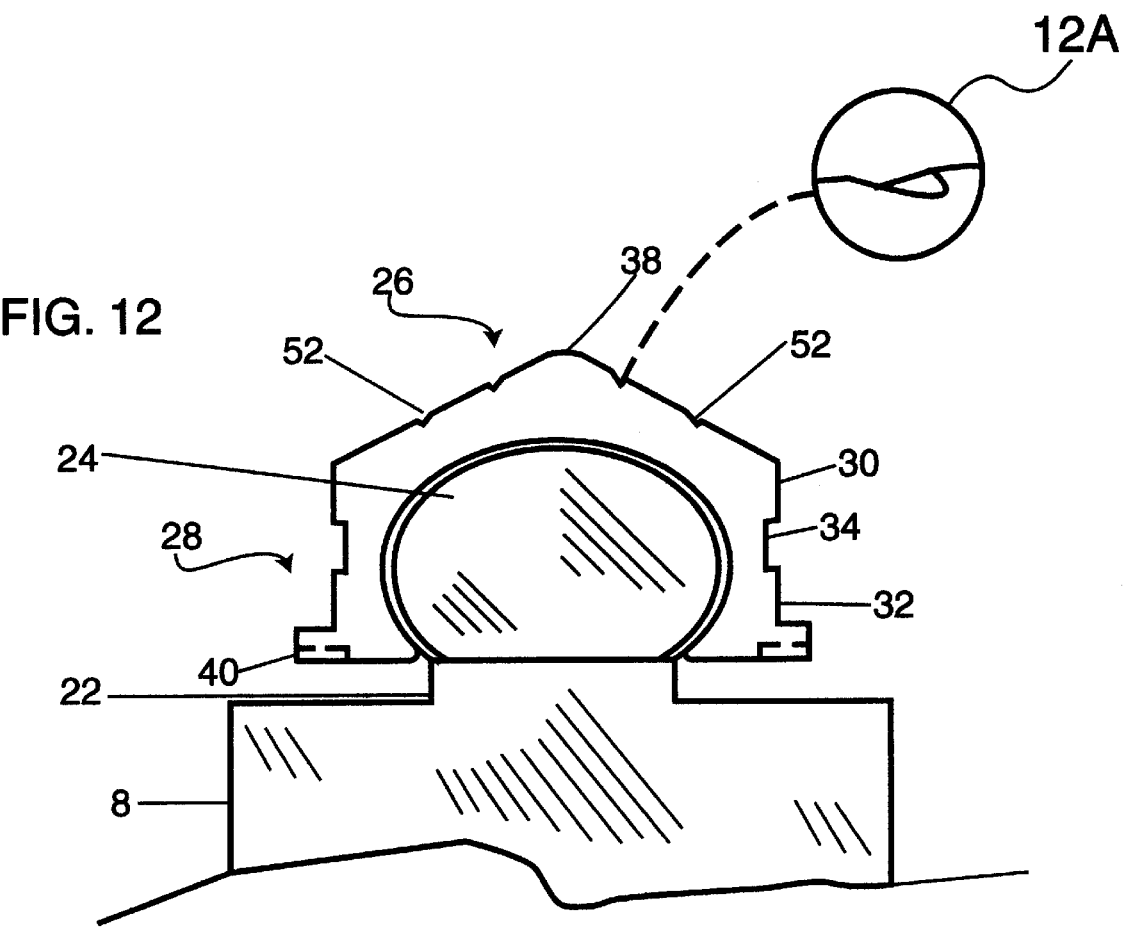
FIG. 12 shows in a partial cross-sectional view of the assembly of the plunger rod and the plastic insert.

FIG. 12 shows in a partial cross-sectional view the assembly of the self-aligning plunger rod 8 and the plastic insert combination 26. The ball portion 24 of the plunger rod tip 20 fits into the cavity or socket 48 of the cone-shaped head 36 and freely moves therein, essentially floating within the cavity or socket. Any external pressure on the plunger rod is directed in an axial direction and does not impact the integrity of the seal formed by an elastomeric plunger head cover (not shown) and the inside wall of a syringe or cartridge barrel (not shown).

As illustrated in FIG. 12, plastic insert 26 is adapted to receive various elastomeric plunger head covers (not shown) by virtue of the design of the plastic insert 26 having a cylindrical recess 34 to hold an oppositely configured elastomeric plunger head. In addition, cylindrical grooves 52 are designed to receive and hold different configurational elastomeric plunger head covers with slight protuberances therein to fit into the grooves 52 of the cone-shaped head 36 of the plastic insert 26.

In use, slots 24a, 24b, 24c and 24d of plunger rod tip 20 are aligned with cylindrical openings 54 in the plastic insert 26. The ball portion 24 of the plunger rod tip is inserted into the cavity 48 of the plastic insert. When inserted, the plunger rod is rotated ¼ turn and is held by tabs 50. To remove the plunger rod from the cavity of the plastic insert, the plunger rod is turned ¼ turn forward or backward.

FIGS. 13–17 show an embodiment of the present invention having a reinforced plunger rod used in combination with the plunger tip and plastic insert above-described, wherein:.

Figure 14:
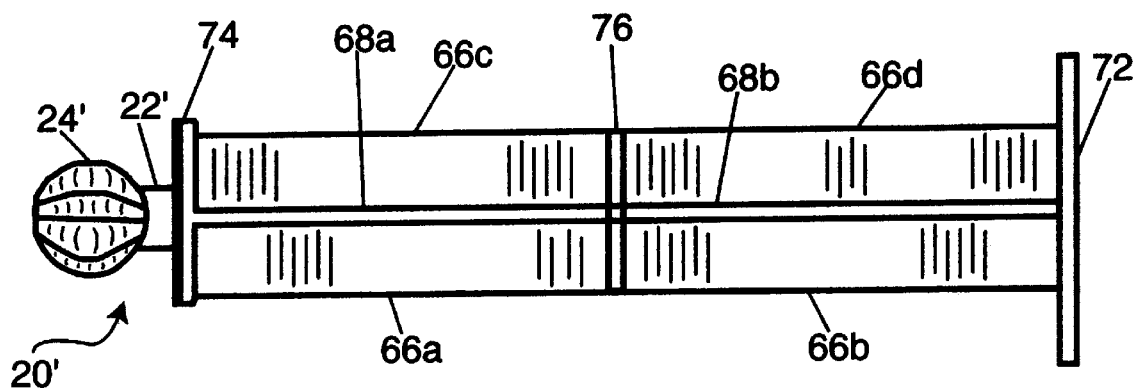
FIG. 14 is a side-elevational view of the reinforced plunger rod shown in FIG. 13.
Figure 15:
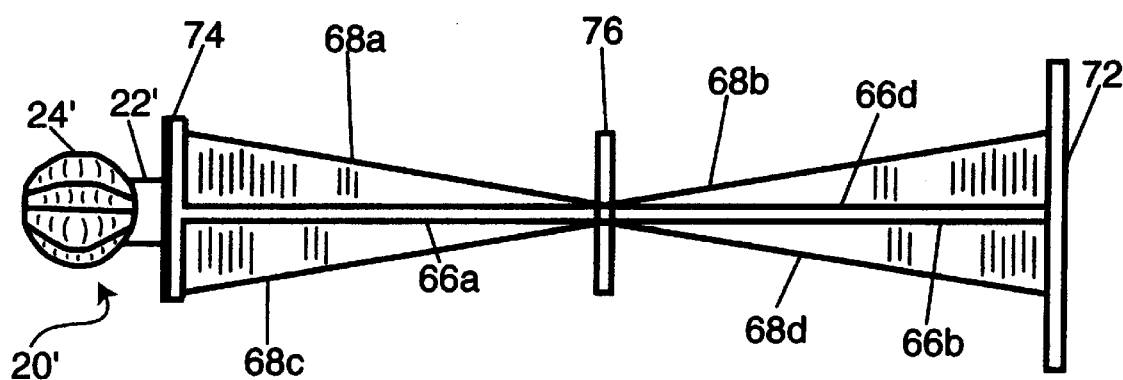
FIG. 15 is another side-elevational view of the reinforced plunger rod shown in FIG. 13 rotated 90° from that shown in FIG. 14.
Figure 16:
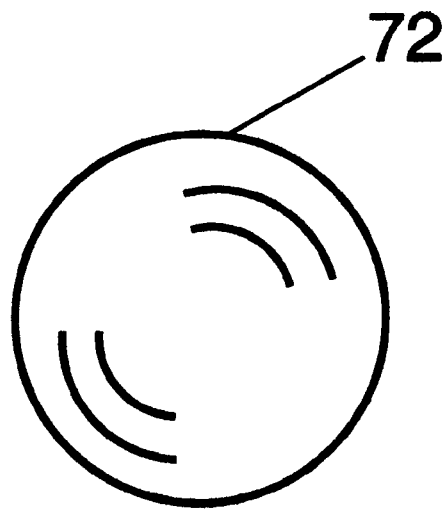
FIG. 16 is a bottom plan view of the reinforced plunger rod shown in FIG. 13.
Figure 17:
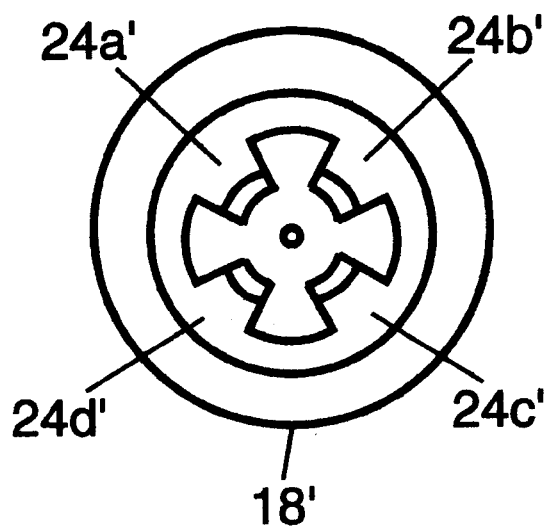
FIG. 17 is the top plan view of the reinforced plunger rod shown in FIG. 13.

FIG. 13 is a perspective view of the reinforced plunger rod;

FIG. 13A is a cross-sectional view of the reinforced plunger rod taken along the line 13A—13A of FIG. 13;

FIG. 13B is another cross-sectional view of the reinforced plunger rod taken along the line 13B—13B of FIG. 13;

FIG. 14 is a side-elevational view of the reinforced plunger rod shown in FIG. 13;

FIG. 15 is another side-elevational view of the reinforced plunger rod shown in FIG. 13 rotated 90° from that shown in FIG. 14;

FIG. 16 is a bottom plan view of the reinforced plunger rod shown in FIG. 13; and FIG. 17 is the top plan view of the reinforced plunger rod shown in FIG. 13.

Self-aligning reinforced plunger rod 60, having a distal end 62 and a proximal end 64 comprises:

longitudinally extending radial vanes 66a and 66b having a rectangular configuration;

longitudinally extending radial vanes 70a and 70b having a triangular configuration;

a thumb rest 72 at the proximal end;

a disc 74 at the distal end;

a central disc 76 located at about the midpoint between thumb rest 72 and disc 74; and a plunger rod tip 20' (generally designated) extending form disc 74 designed to engage a plastic insert.

Plunger rod tip 20' is integral with disc 74 and comprises: a neck portion 22', and a ball portion 24', the ball portion having slots 24a', 24b', 24c' and 24d' therein extending axially from the neck portion.

The reinforced plunger rod 60 is used in combination with plastic insert 26 which is shown and described in FIGS. 9–12.

Figure 19:
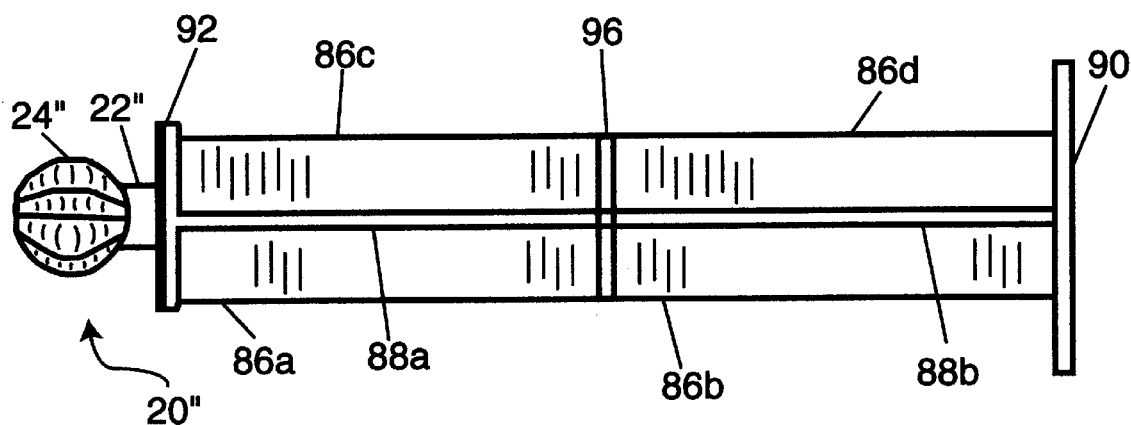
FIG. 19 is a side-elevational view of the reinforced plunger rod shown in FIG. 18.
Figure 20:
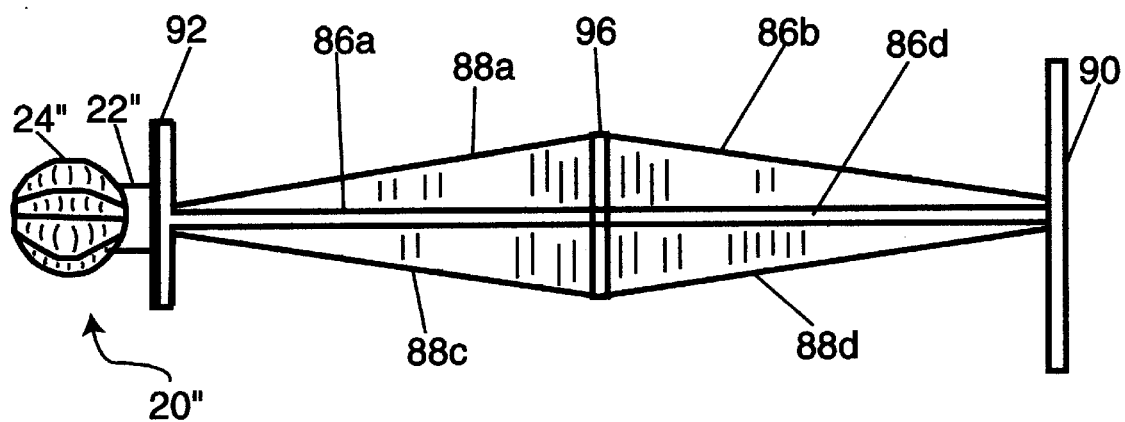
FIG. 20 is another side-elevational view of the reinforced plunger rod shown in FIG. 18 rotated 90° from that shown in FIG. 19.
Figure 21:
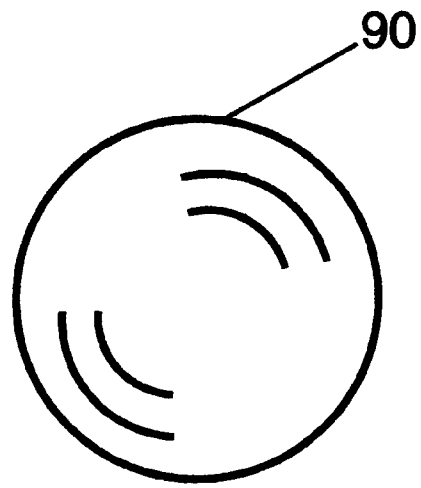
FIG. 21 is a bottom plan view of the reinforced plunger rod shown in FIG. 18.
Figure 22:
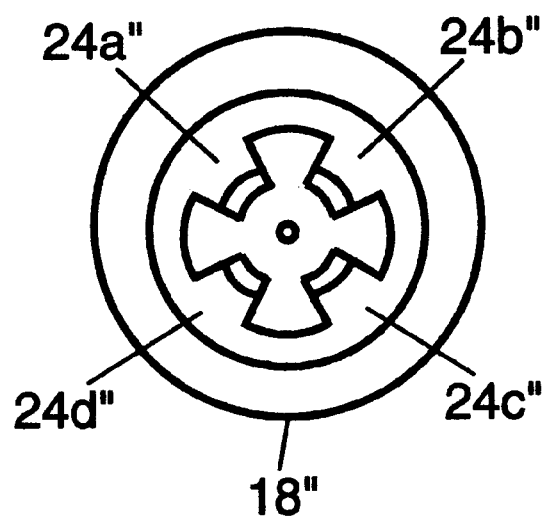
FIG. 22 is a top plan view of the reinforced plunger rod shown in FIG. 18.

FIGS. 18–22 show another embodiment of the present invention having a reinforced plunger rod used in combination with the plunger tip and plastic insert above-described, wherein:

FIG. 18 is a perspective view of the reinforced plunger rod;

FIG. 18A is a cross-sectional view of the reinforced plunger rod taken along the line 18A—18A of FIG. 18;

FIG. 18B is a cross-sectional view of the reinforced plunger rod taken along the line 18B—18B of FIG. 18;

FIG. 19 is a side-elevational view of the reinforced plunger rod shown in FIG. 18;

FIG. 20 is another side-elevational view of the reinforced plunger rod shown in FIG. 18 rotated 90° from that shown in FIG. 19;

FIG. 21 is a bottom plan view of the reinforced plunger rod shown in FIG. 18; and FIG. 22 is a top plan view of the reinforced plunger rod shown in FIG. 18.

Plunger rod 80 having a distal end 82 and a proximal end 84 comprises:

longitudinal radially extending vanes 86a, 86b, (86c and 86d are hidden in FIG. 18) having a rectangular configuration;

longitudinal radially extending vanes 88a, 88b, 88c and 88d having triangular configuration;

thumb rest 90 at the proximal end 84 of the plunger rod 80;

a disc 92 at the distal end 82 of the plunger rod;

plunger rod tip 94 extending from disc 92 designed to engage a plastic insert; and a central disc 96 located at about the midpoint between thumb rest 90 and disc 92.

Central disc 96 supports the rectangular vanes and the triangular vanes and is integral therewith to provide dimensional stability to the plunger rod. Cross sectional view FIG. 18A taken along the line 18A—18A of FIG. 18 illustrates that at about the midpoint of the plunger rod the rectangular and triangular vanes are about equal in size in the radial direction, however, while the rectangular vanes connecting to the central disc 96, disc 92 and thumb rest 90 maintain their rectangular configuration, the triangular vanes diminish in size in the radial direction as they approach disc 92 and thumb rest 90. As shown, the triangular vanes merge with the rectangular vanes at disc 92 and thumb rest 90. Cross-sectional view of the plunger rod in FIG. 18B, taken along the line 18B—18B of FIG. 18 shows that triangular vanes 88a, 88b, 88c and 88d diminish to a small size and merge with rectangular vanes 86a and 86b at disc 92 and thumb rest 90.

FIG. 19 shows the plunger rod of FIG. 18 in a side-elevational view where triangular vanes 88a and 88b are at the center of the Figure, and rectangular vanes 86a, 86b, 86c and 86d are at the sides of the Figure.

FIG. 20 is another side-elevational view of the plunger rod of FIG. 18 rotated 90° from that shown in FIG. 19. The triangular vanes 88a, 88b, 88c and 88d are at the sides of the Figure and rectangular vanes 86a and 86d are at the center thereof.

FIGS. 21 and 22 show respectively the bottom and top plan views of the plunger rod.

Plunger rod tip 20" is integral with disc 92 and comprises:
a neck portion 22", and a ball portion 24", the ball portion having slots 24a", 24b", 24c" and 24d" therein extending axially from the neck portion.

The reinforced plunger rod 80 is used in combination with plastic insert 26 which is shown and described in FIGS. 9–12.

Figure 23:
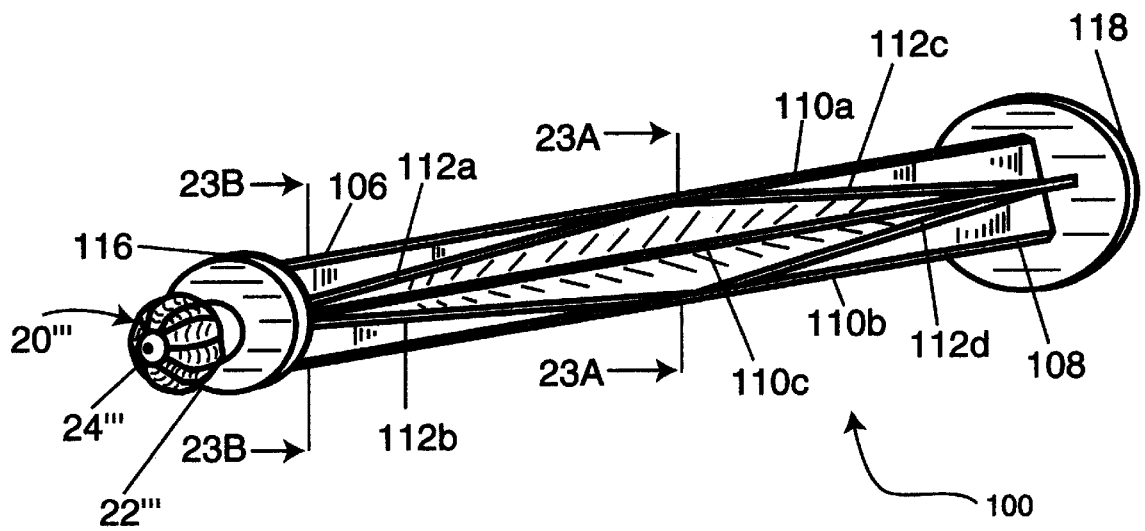
FIG. 23 is a perspective view of another embodiment of the present invention showing a reinforced plunger rod.
Figure 23B:
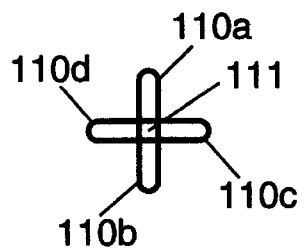
FIG. 23B is a cross-sectional view of the embodiment taken along the line 23B—23B.
Figure 23A:
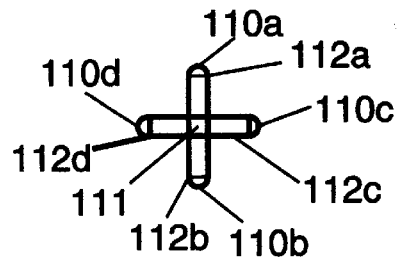
FIG. 23A is a cross-sectional view of the embodiment taken along the line 23A—23A of FIG. 23.

Reference is now being made to the fourth embodiment of the present invention shown in FIGS. 23–27. The plunger rod, generally designated by the numeral 100, includes four longitudinal radially extending rectangular vanes, 110a, 110b, 110c and 110d as best seen in FIGS. 23, 23A and 23B. These vanes meet at a center line or axis 111. The vanes are integral with each other at the axis. At the distal end 106 the vanes terminate in a disc 116; at the proximal end 108 the vanes terminate in a thumb rest 118. In addition to the four longitudinal radially extending rectangular vanes, which constitute a typical prior art plunger rod, the present invention incorporates reinforcing or supporting vanes in the plunger rod which comprise: a first pair of longitudinal radially extending supporting vanes; and a second pair of longitudinally extending supporting vanes. Both the first pair and the second pair of longitudinally extending supporting vanes are connected to disc 116 at the distal end 106 and to the thumb rest 118 at the proximal end 108 of plunger rod 100.

FIG. 23 A shows a cross-sectional view of plunger rod 100 taken along the line 23A—23A of FIG. 23 wherein: the numerals 110a, 110b, 110c and 110d denote the longitudinal radially extending rectangular vanes; the numerals 112a, 112b, 112c and 112d denote the longitudinal radially extending supporting vanes; and the numeral 111 denotes the central axis at which the longitudinal extending rectangular vanes meet.

Figure 24:
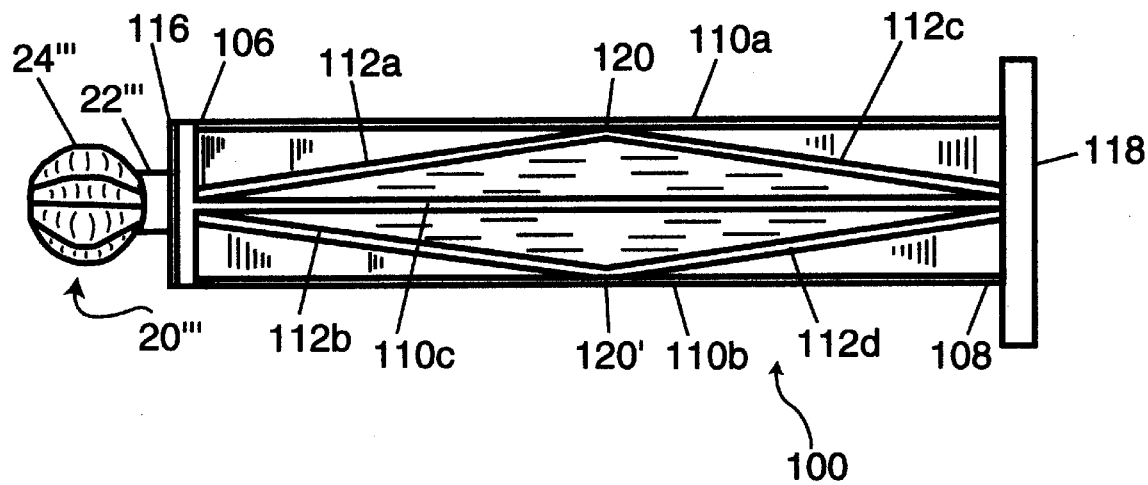
FIG. 24 is a side-elevational view of the embodiment shown in FIG. 23.

As shown in FIG. 24, the first pair of longitudinal radially extending supporting vanes 112a and 112c and 112b and 112d form two obtuse triangles with the longitudinal radially extending rectangular vanes 110c, wherein the obtuse angles of the triangles are at or approximately at the midpoints 120 and 120' between disc 116 and thumb rest 118.

Figure 24A:
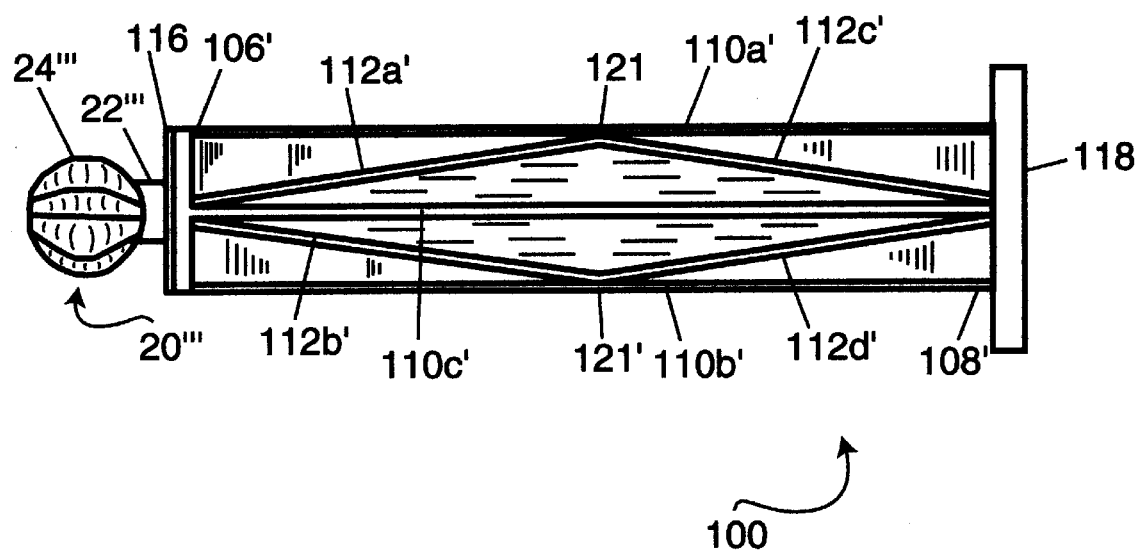
FIG. 24A is another side-elevational view of the embodiment shown in FIG. 23 rotated 180° from that shown in FIG. 24.

When side-elevational view of plunger rod 100 shown in FIG. 24 is rotated 180°, the opposite side, or mirror image side, is shown thereof in FIG. 24A wherein like numbers correspond with numerals shown in FIG. 24 and are distinguished therefrom by the marks' or".

Figure 25:
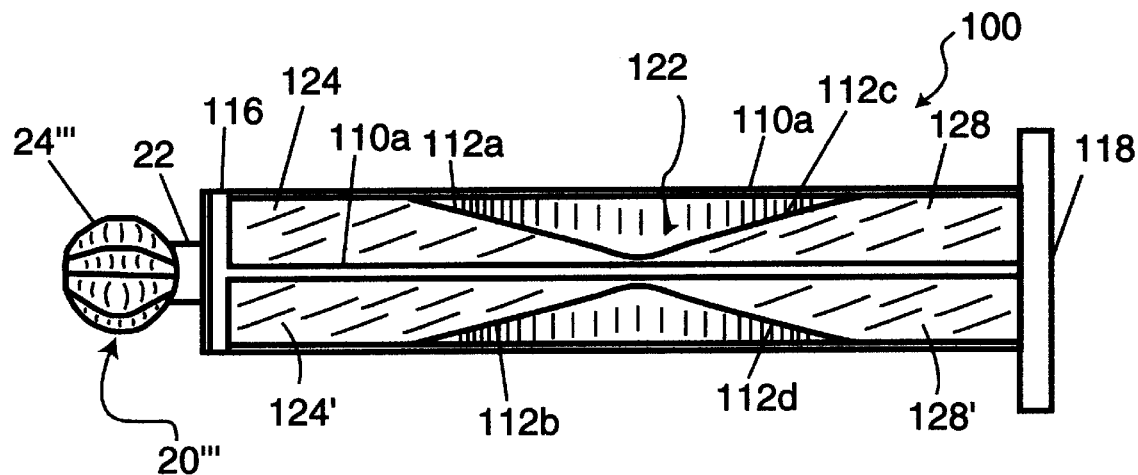
FIG. 25 is another side-elevational view of the embodiment shown in FIG. 23 rotated 90° from that shown in FIG. 24.

Turning now to another side-elevational view of plunger rod 100, FIG. 25 shows a side-elevational view of plunger rod 100 rotated 90° from that of the side-elevational view shown in FIG. 24. As shown in FIG. 25, first pair of longitudinal radially extending supporting vanes: 112a and 112c and 112b and 112d together form a two-dimensional hourglass-shape surface. Longitudinal radially extending rectangular vane 110a runs through the center portion of the radially extending two-dimensional hourglass-shape surface connecting disc 116 and thumb rest 118. The hourglass-shape surface constricts into a channel generally designated with the numeral 122 at or approximately at the midpoint between disc 116 and thumb rest 118. Distal end 124 and 124' and proximal end 128 and 128' of the hourglass-shape surface extend to disc 116 and thumb rest 118 and merge with longitudinal radially extending rectangular vane 110a.

Figure 25A:
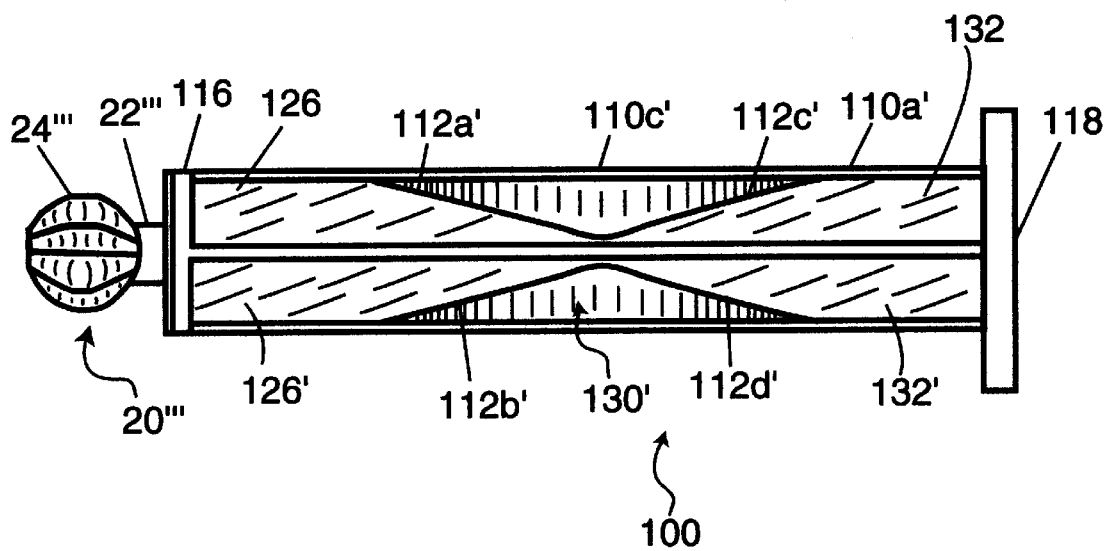
FIG. 25A is another side-elevational view of the embodiment shown in FIG. 23 rotated 90° from that shown in FIG. 24A.
Figure 26:
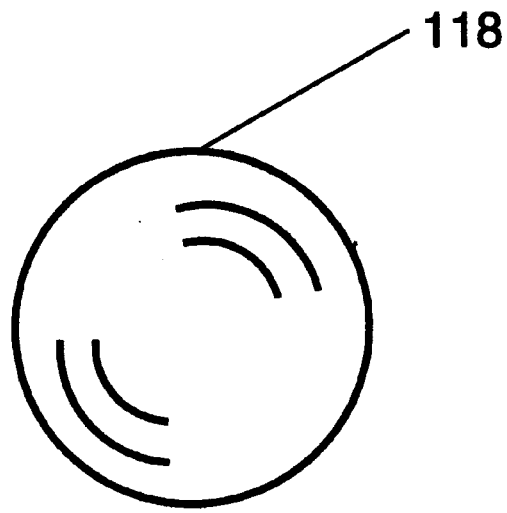
FIG. 26 is a bottom plan view of the embodiment shown in FIG. 23.

When the side-elevational view of plunger rod 100 shown in FIG. 25 is rotated 180°, the opposite side, or mirror image side of the plunger rod, is shown in FIG. 25A wherein: the numeral 128' denotes a channel into which the hourglass-shape surface constricts; the numerals 126 and 126' denote the distal end of the hourglass-shape surface; and the numerals 132 and 132' denote the proximal end of the hourglass-shape surface.

Figure 27:
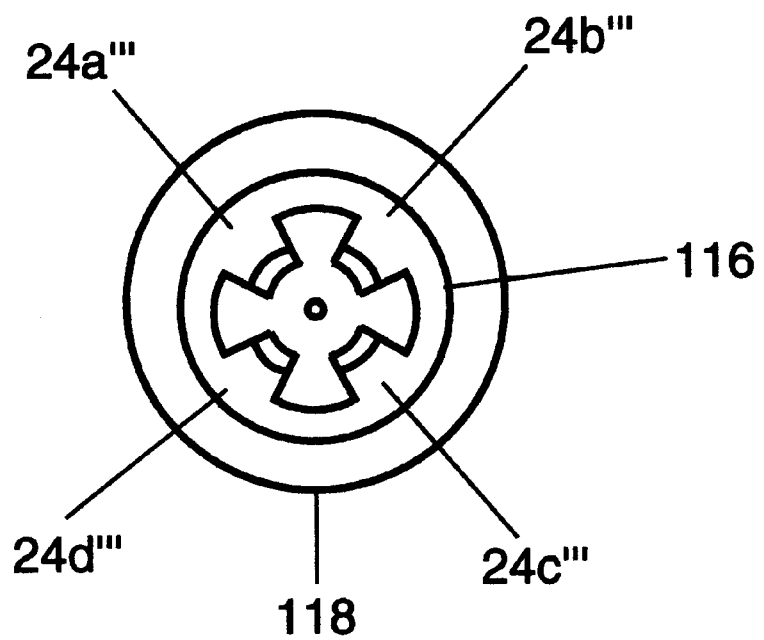
FIG. 27 is a top plan view of the embodiment shown in FIG. 23.

The plunger rod tip 20''' is integral with disc 116 and comprises:
a neck portion 22''' and a ball portion 24''', the ball portion having slots 24a''', 24b''', 24c''' and 24d''' therein as shown in FIG. 27.

The reinforced plunger rod 100 is used in combination with plastic insert 26 which is shown and described in FIGS. 9–12.

Reference is now being made to the fifth embodiment of the present invention shown in FIGS. 28–32. The plunger rod, generally designated by the numeral 140, includes four longitudinal radially extending vanes 150a, 150b, 150c and 150d. These vanes meet at the center line or axis 151. The vanes are integral with each other at the axis. At the distal end 146 the vanes terminate in a disc 156; at the proximal end the vanes terminate in a thumb rest 158. In addition to the four longitudinal radially extending rectangular vanes, which constitute a typical prior art plunger rod, the present invention incorporates reinforcing or supporting vanes in the plunger rod which comprise: a first pair of longitudinal radially extending supporting vanes; and a second pair of longitudinal extending supporting vanes. Furthermore, at about the midpoint between end disc 156 and thumb rest 158, an additional reinforcing feature is included in the form of a central disc 159. Both of the first pair and the second pair of longitudinal radially extending supporting vanes are connected to disc 156 at the distal end, to central disc 159, and thumb rest 158.

Figure 28:
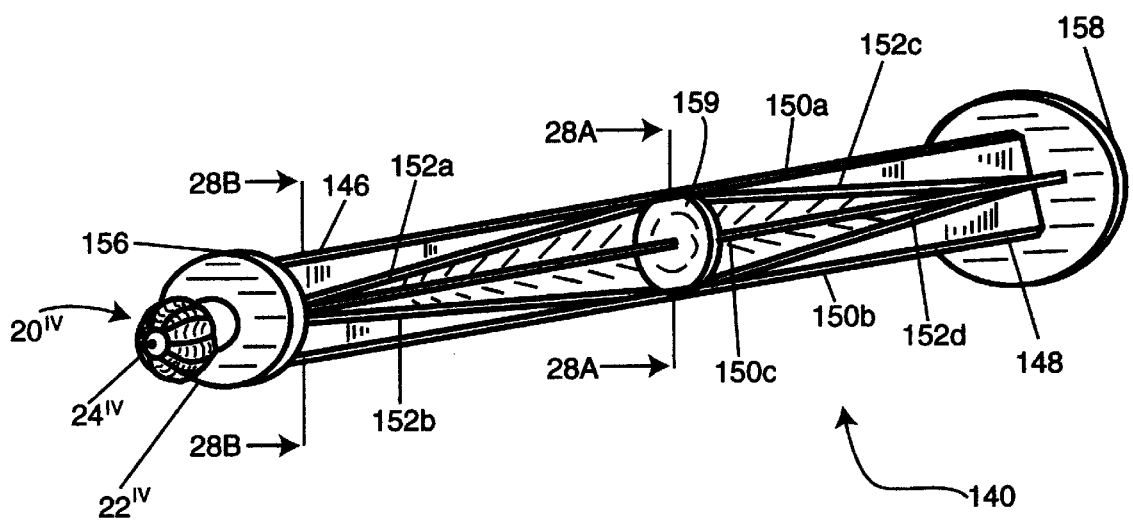
FIG. 28 is a perspective view of another embodiment of the present invention showing a reinforced plunger rod which incorporates a central disc.
Figure 28B:
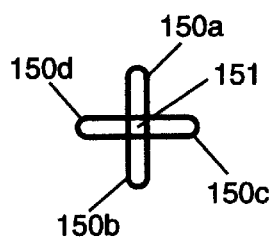
FIG. 28B is a cross-sectional view of the embodiment taken along the line 28B—28B of FIG. 28.
Figure 28A:
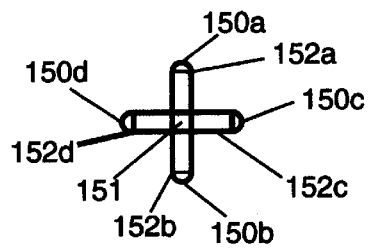
FIG. 28A is a cross-sectional view of the embodiment taken along the line 28A—28A of FIG. 28.

FIG. 28A shows a cross-sectional view of plunger rod 140 taken along the line 28A—28A of FIG. 28 wherein: the numerals 150a, 150b, 150c and 150d denote the longitudinal radially extending rectangular vanes; the numerals 152a, 152b, 152c and 152d denote the longitudinal radially extending supporting vanes; and the numeral 151 denotes the central axis at which the longitudinal extending rectangular vanes meet.

Figure 29:
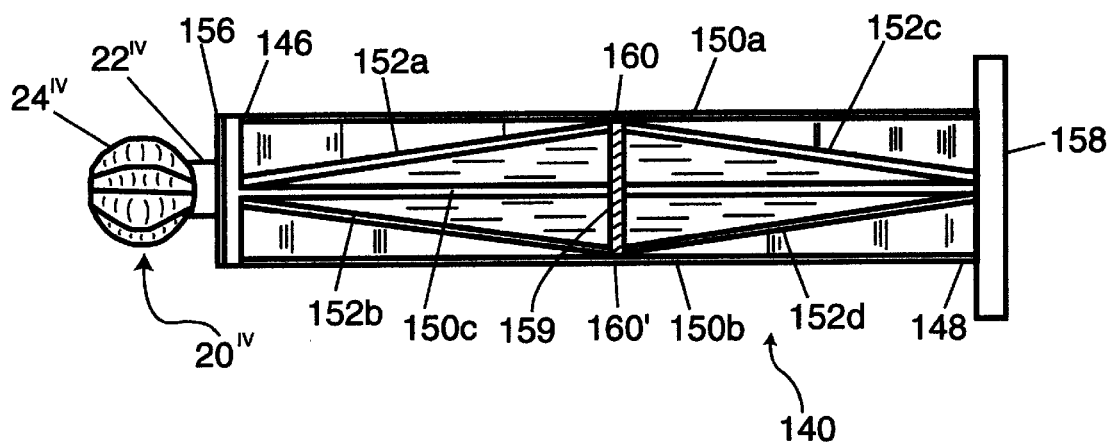
FIG. 29 is a side-elevational view of the embodiment shown in FIG. 28.

As shown in FIG. 29, the first pair of longitudinal radially extending supporting vanes 152a and 152c and 152b and 152d form two obtuse triangles with the longitudinal radially extending rectangular vane 150c, wherein the obtuse angles of the triangles are at or approximately at the midpoints 160 and 160' between disc 156 and thumb rest 158. Central disc 159 is also at or approximately at this midpoint supporting the longitudinal radially extending supporting vanes.

Figure 29A:
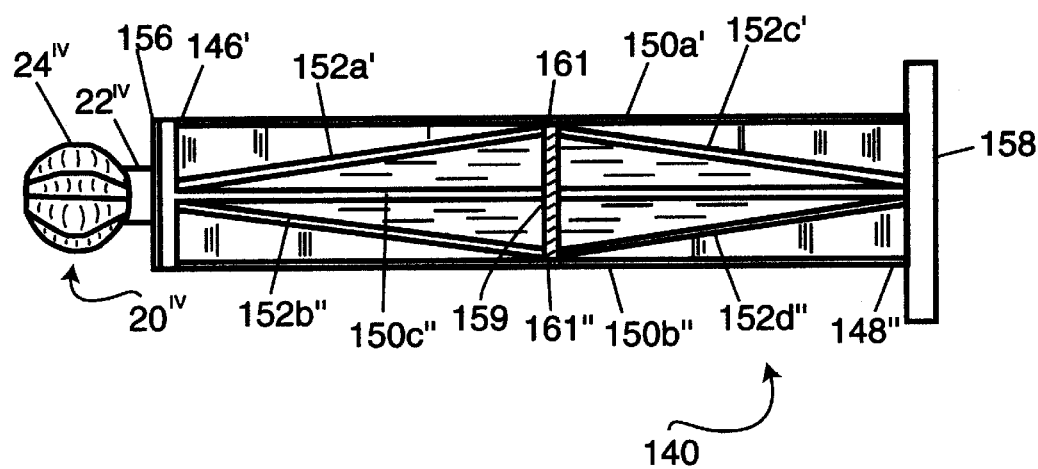
FIG. 29A is another side-elevational view of the embodiment shown in FIG. 28 rotated 180° from that shown in FIG. 29.

When side-elevational view of plunger rod 140 shown in FIG. 29 is rotated 180°, the opposite side, or mirror image side, is shown thereof in FIG. 29A wherein like numbers correspond with numerals shown in FIG. 29 and are distinguished therefrom by the marks' or".

Figure 30:
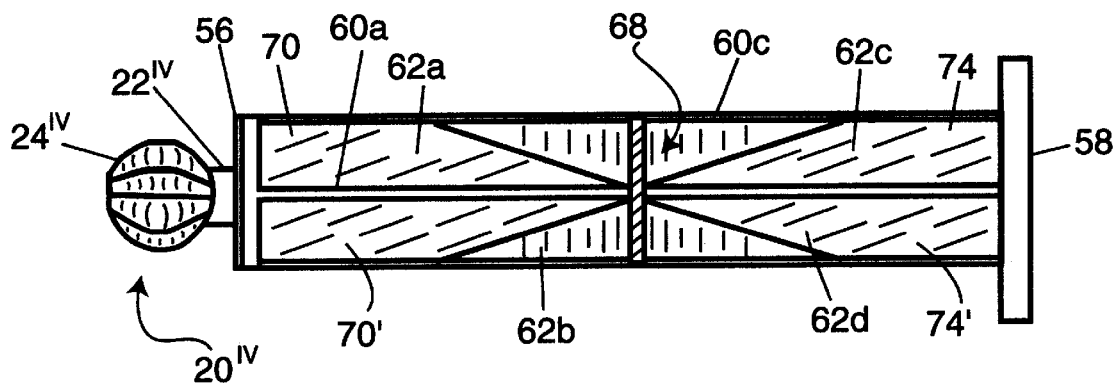
FIG. 30 is another side-elevational view of the embodiment shown in FIG. 28 rotated 90° from that shown in FIG. 29.

Turning now to another side-elevational view of plunger rod 140, FIG. 30 shows a side-elevational view of plunger rod 140 rotated 90° from that of the side-elevational view shown in FIG. 29. As shown in FIG. 30, first pair of longitudinal radially extending supporting vanes: 152*a* and 152*c*; and 152*b* and 152*d* together form a two-dimensional hourglass-shape surface. Longitudinal radially extending rectangular vane 150*a* runs through the center portion of the radially extending two-dimensional hourglass-shape surface connecting disc 156, central disc 159, and thumb rest 158. The hourglass-shape surface constricts into a channel generally designated with the numeral 162 at or approximately at the midpoint between disc 156 and thumb rest 158. The central disc 159 is located at or approximately at this midpoint. Distal end 164 and 164' and proximal end 168 and 168' of the hourglass-shape surface extend to disc 156 and thumb rest 158 and merge with longitudinal radially extending rectangular vane 150*a*.

Figure 30A:
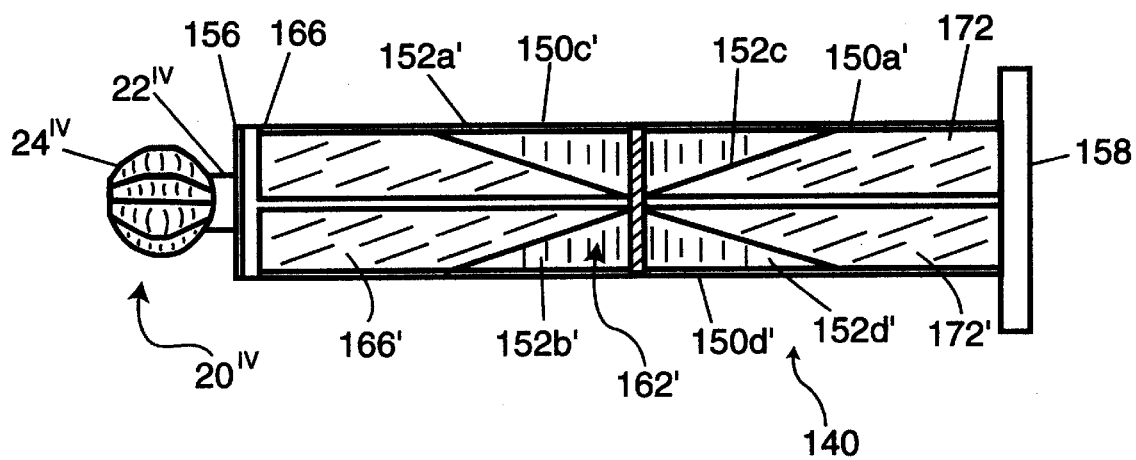
FIG. 30A is another side-elevational view of the embodiment shown in FIG. 28 rotated 90° from that shown in FIG. 29A.
Figure 31:
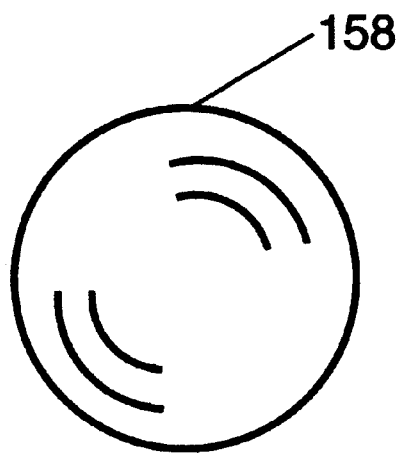
FIG. 31 is a bottom plan view of the embodiment shown in FIG. 28.

When the side-elevational view of plunger rod 140 shown in FIG. 30 is rotated 180°, the opposite side, or mirror image side of the plunger rod, is shown in FIG. 30A wherein: the numeral 162' denotes a channel into which the hourglass-shape surface constricts; the numerals 166 and 166' denote the distal end of the hourglass-shape surface; and the numerals 172 and 172' denote the proximal end of the hourglass-shape surface.

Figure 32:
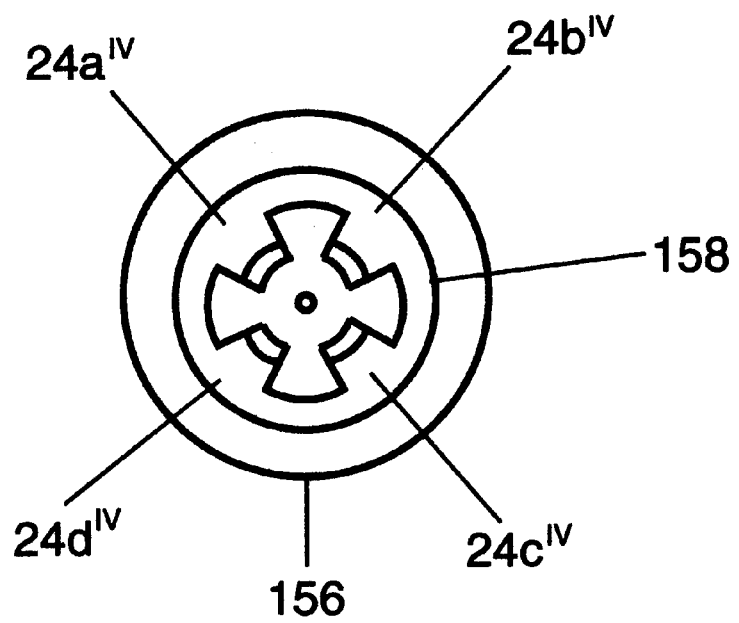
FIG. 32 is a top plan view of the embodiment shown in FIG. 28.

The plunger rod tip, generally shown as 20$^{iv}$ in FIGS. 28–30A is shown specifically in FIG. 32 and comprises:

a neck portion 22$^{iv}$ and a ball portion 24$^{iv}$, the ball portion having slots 24*a*$^{iv}$, 24*b*$^{iv}$, 24*c*$^{iv}$ and 24*d*$^{iv}$ therein as shown in FIG. 32.

The reinforced plunger rod 140 is used in combination with plastic insert 26 which is shown and described in FIGS. 9–12.

The plunger rods and the plastic insert assemblies of the present invention are made by injection molding, well-known in the art, using thermoplastic materials. Polypropylene, polyethylene and blends thereof are preferred for providing strength to the plunger rods. However, other polymers, such as polystyrenes, polyesters and polycarbonates may also be used.

LIST OF REFERENCE NUMBERS USED

PRIOR ART

| | |
|---|---|
| Plunger rod | 1 |
| Distal end of plunger rod | 2 |
| Proximal end of plunger rod | 3 |
| Vanes of plunger rod | 4a, 4b, 4c & 4d |
| Thumb rest | 5 |
| Disc | 6 |
| Screw threaded member | 7 |

PRESENT INVENTION (FIRST EMBODIMENT)

| | |
|---|---|
| Self-aligning plunge rod (generally designated) | 8 |
| Distal end of self-aligning plunger rod | 10 |
| Proximal end of self-aligning plunger rod | 12 |
| Longitudinal, radially extending vanes | 14a, 14b, 14c & 14d |
| Thumb rest at the proximal end | 16 |
| Disc at distal end | 18 |
| Plunger rod tip (generally designated) | 20 |

-continued

LIST OF REFERENCE NUMBERS USED

| | |
|---|---|
| Neck portion of plunger rod tip | 22 |
| Ball portion of plunger rod tip | 24 |
| Slots in ball portion | 24a, 24b, 24c & 24d |
| Plastic insert (generally designated) | 26 |
| Cylindrical shaft of plastic insert (generally designated) | 28 |
| Distal end of cylindrical shaft | 30 |
| Proximal end of cylindrical shaft | 32 |
| Cylindrical recess or groove in cylindrical shaft | 34 |
| Cone-shaped head | 36 |
| Zenith of cone-shaped head | 38 |
| Cylindrical flange of cylindrical shaft | 40 |
| First cylindrical rim on the underside of flange 40 | 42 |
| Second cylindrical rim | 44 |
| Plurality of reinforcing rods | 46 |
| Cavity inside of the cone-shaped head | 48 |
| Plurality of tabs extending into cavity 48 | 50 |
| Cylindrical notches in the outside surface of the ball portion of plastic insert | 52 |
| Cylindrical openings in the inside surface of plastic insert | 54 |

PRESENT INVENTION (SECOND EMBODIMENT)

| | |
|---|---|
| Self-aligning plunger rod (generally designated) | 60 |
| Distal end of self-aligning plunger rod | 62 |
| Proximal end of self-aligning plunger rod | 64 |
| Longitudinal, radially extending vanes having a rectangular configuration | 66a, 66b, 66c & 66d |
| Longitudinal, radially extending vanes having a triangular configuration | 68a, 68b, 68c, 68d, 70a & 70b |
| Thumb rest | 72 |
| Disc at the distal end of plunger rod | 74 |
| Central disc | 76 |
| Plunger rod tip (generally designated) | 20' |
| Neck portion of plunger rod tip | 22' |
| Ball portion of plunger rod tip | 24' |
| Slots in ball portion | 24a', 24b', 24c' & 24d' |

PRESENT INVENTION (THIRD EMBODIMENT)

| | |
|---|---|
| Plunger rod | 80 |
| Distal end of plunger rod | 82 |
| Proximal end of plunger rod | 84 |
| Longitudinal radially extending vanes having a rectangular configuration | 86a, 86b, 86c & 86d |
| Longitudinal radially extending vanes having a triangular configuration | 88a, 88b, 88c & 88d |
| Thumb rest | 90 |
| Disc at distal end | 92 |
| Central disc | 96 |
| Plunger rod tip (generally designated) | 20" |
| Neck portion of plunger rod tip | 22" |
| Ball portion of plunger rod tip | 24" |
| Slots in ball portion | 24a", 24b", 24c" & 24d" |

PRESENT INVENTION (FOURTH EMBODIMENT)

| | |
|---|---|
| Plunger rod, generally designated | 100 |
| Distal end of plunger rod | 106, 106' |
| Proximal end of plunger rod | 108 |
| Longitudinal radially extending rectangular vanes | 110a, 110b, 110c & 110d |
| Center line or axis | 111 |
| Longitudinal radially extending supporting vanes | 112a, 112b, 112c & 112d, 112a', 112b', 112c' & 112d' |
| Disc | 116 |
| Thumb rest | 118 |
| Obtuse angles of the triangles | 120, 120', 121 & 121' |
| Channel in hourglass-shape surface, generally designated | 122, 130 |

-continued

LIST OF REFERENCE NUMBERS USED

| | |
|---|---|
| Distal end of hourglass-shape surface | 124, 124', 126 & 126' |
| Proximal end of hourglass-shape surface | 128, 128', 132 & 132' |
| PRESENT INVENTION (FIFTH EMBODIMENT) | |
| Plunger rod, generally designated | 140 |
| Distal end of plunger rod | 146, 146' |
| Proximal end of plunger rod | 148, 148' |
| Longitudinal radially extending rectangular vanes | 150a, 150b, 150c & 150d, 150a', 150b', 150c' & 150d' |
| Center line or axis | 151 |
| Longitudinal radially extending supporting vanes | 152a, 152b, 152c & 152d, 152a', 152b', 152c' & 152d' |
| Disc at distal end | 156 |
| Thumb rest | 158 |
| Central disc | 159 |
| Obtuse angles of the triangles | 160, 160', 161 & 161' |
| Channel in hourglass-shape surface, generally designated | 162, 162' |
| Distal end of hourglass-shape surface | 164, 164', 166 & 166' |
| Proximal end of hourglass-shape surface | 168, 168', 172 & 172' |
| Plunger rod tip, generally designated | $20^{iv}$ |
| Neck portion of plunger rod tip | $22^{iv}$ |
| Ball portion of plunger rod tip | $24^{iv}$ |
| Slots in ball portion | $24a^{iv}$, $24b^{iv}$, $24c^{iv}$, & $24d^{iv}$ |

Various modification of the present invention will become apparent to those skill in the art. The invention is intended to include such modifications to be limited only by the scope of the claims.

What is claimed is:

1. A self-aligning reinforced plunger rod and non-elastomeric plastic plunger insert assembly for use with an elastomeric plunger in a cartridge or syringe barrel for manual or power-assisted withdrawing of fluid from a site or expelling fluid from the cartridge or syringe barrel:
   a) a plunger rod having a first, second, third and fourth sides, a distal end and a proximal end comprising:
      an end disc at the distal end;
      a plunger rod tip extending from said end disc adapted to engage a plastic plunger insert, said plunger rod tip comprising a neck portion and a ball portion, said ball portion having slots therein extending axially from said neck portion;
      a thumb rest at the proximal end for facilitating exertion of external pressure on the plunger rod;
      a central disc at about the midpoint between the end disc and the thumb rest to provide additional reinforcement between the end disc and the thumb rest;
      four longitudinal radially extending rectangular vanes spaced about 90° from each other and connected to said end disc, to said central disc, and to said thumb rest;
   on the first side of said plunger rod:
      a first pair of longitudinal radially extending reinforcing vanes;
      a second pair of longitudinal radially extending reinforcing vanes, both the first pair and the second pair of longitudinal radially extending reinforcing vanes being connected to said end disc, to said central disc, and to said thumb rest;
   on the third side opposite to said first side of said plunger rod;
      a first pair of longitudinal radially extending reinforcing vanes;
      a second pair of longitudinal radially extending reinforcing vanes, both said first pair and said second pair of longitudinal radially extending reinforcing vanes being connected to said end disc, to said central disc, and to said thumb rest,
   wherein:
      each of said first and second pairs of the longitudinal radially extending reinforcing vanes on the first side of said plunger rod, and each of said first and second pairs of the longitudinal radially extending reinforcing vanes on the third side of said plunger rod forms an obtuse triangle with one of the longitudinal radially extending rectangular vanes, wherein the obtuse angle of the so-formed triangle is at the midpoint between said end disc and said thumb rest;
   on the second side of said plunger rod:
      a first pair of longitudinal radially extending reinforcing vanes forming a two-dimensional hourglass-shape surface extending from said end disc to said central disc, and from said central disc to said thumb rest; and
   on the fourth side of said plunger rod:
      a second pair of longitudinal radially extending reinforcing vanes forming a two-dimensional hourglass-shape surface extending from said end disc to said central disc, and from said central disc to said thumb rest;
   b) a non-elastomeric plastic plunger insert comprising:
      a cylindrical shaft having a distal end and a proximal end;
      a cone-shaped head extending from the distal end of said cylindrical shaft having an inside surface and an outside surface;
      a cavity in the cone-shaped head defined by a cylindrical rim and the inside surface of the cone-shaped head;
      a plurality of tabs extending from the cylindrical rim into the cavity; and
      a plurality of notches or openings between the tabs designed to receive the slotted ball portion of said plunger rod tip.

2. The self-aligning reinforced plunger rod and non-elastomeric plastic plunger insert assembly of claim 1 wherein said cone-shaped head terminates in a zenith.

3. The self-aligning reinforced plunger rod and non-elastomeric plastic plunger insert assembly of claim 1 wherein the number of tabs in said non-elastomeric plastic insert matches the number of slots in said ball portion of said plunger rod tip.

4. The self-aligning reinforced plunger rod and non-elastomeric plastic plunger insert assembly of claim 3 wherein the number of tabs in the non-elastomeric plastic insert is 2–10 and the number of slots in the ball portion of said plunger rod is 2–10.

5. The self-aligning reinforced plunger rod and non-elastomeric plastic plunger insert assembly of claim 1 wherein said outside surface of said cone-shaped head is provided with at least one cylindrical groove for engagement with a protuberance in an elastomeric plunger.

6. The self-aligning reinforced plunger rod and non-elastomeric plastic plunger insert assembly of claim 1 made of a thermoplastic polymer.

7. The self-aligning reinforced plunger rod and non-elastomeric plastic plunger insert assembly of claim 1 made of polypropylene, polyethylene or blends thereof.

8. The self-aligning reinforced plunger rod and non-elastomeric plastic plunger insert assembly of claim 1 made of a polymeric material selected from the group consisting of polystyrenes, polyesters and polycarbonates.

9. The self-aligning reinforced plunger rod and non-elastomeric plastic plunger insert assembly of claim 1 made by injection molding.

* * * * *